United States Patent [19]

Friedman

[11] Patent Number: 5,385,734

[45] Date of Patent: Jan. 31, 1995

[54] HORSERADISH PREPARATION FOR THE TREATMENT OF NASAL AND SINUS DYSFUNCTION

[75] Inventor: William H. Friedman, St. Louis, Mo.

[73] Assignee: Horseradish Spray, Inc., St. Louis, Mo.

[21] Appl. No.: 68,998

[22] Filed: May 27, 1993

Related U.S. Application Data

[62] Division of Ser. No. 844,107, Mar. 2, 1992, Pat. No. 5,248,504.

[51] Int. Cl.[6] ............... A01N 65/00; A61K 35/78; A61K 9/14
[52] U.S. Cl. ............... 424/434; 424/195.1; 424/489; 514/951
[58] Field of Search ............ 424/195.1, 434, 489; 514/951; 426/615

[56] References Cited

U.S. PATENT DOCUMENTS 4,782,023  11/1988  Anawis et al. ............ 435/188
5,114,969  5/1992  Chung et al. ............ 514/514

OTHER PUBLICATIONS

Fan-Yung et al, "Dispersion Characteristics of Vegetable Juices", Izvestiya Vysshikh Uchebnykh Zavedenii, Pishcheyaya Tekhnologiya 1980, No. 2, 138–139, Abstract only.

Primary Examiner—Thurman K. Page
Assistant Examiner—Carlos Azpuru
Attorney, Agent, or Firm—Bryan Cave

[57] ABSTRACT

A method of treatment for nasal and sinus dysfunction is disclosed comprising topically applying a horseradish, sinigrin or allyl isothiocyanate preparation to affected mucosa. Preparations for the treatment of nasal and sinus dysfunction are also disclosed, including preparations of horseradish, sinigrin and allyl isothiocyanate.

10 Claims, No Drawings

HORSERADISH PREPARATION FOR THE TREATMENT OF NASAL AND SINUS DYSFUNCTION

CROSS-REFERENCE TO RELATED APPLICATION

This application is a division of U.S. application Ser. No. 07/844,107, filed Mar. 2, 1992, now U.S. Patent No. 5,248,504, granted Sep. 28, 1993.

FIELD OF THE INVENTION

This invention relates to a method of treatment for nasal and sinus dysfunction comprising topically applying a horseradish, sinigrin or allyl isothiocyanate preparation to affected mucosa. The invention also relates to preparations for the treatment of nasal and sinus dysfunction, including preparations of horseradish, sinigrin and allyl isothiocyanate.

BACKGROUND OF THE INVENTION

Many people suffer from nasal and sinus dysfunction. Examples of nasal and sinus dysfunction include allergic and vasomotor inflammatory conditions of nasal mucous membranes, sinugenic headaches, post nasal discharge, and the like.

Nasal sprays have been used in the treatment of such nasal and sinus dysfunctions, but are not without drawbacks. For instance, common nasal sprays containing sympatho-mimetic compounds, and over-the-counter remedies containing phenylephrine hydrochloride, oxymetazoline hydrochloride, or xylometazoline are generally considered to be harmful when used over long periods of time because they cause damage to nasal mucosal ciliary function, and they cause rebound mucosal thickening leading to nasal congestion. The manufacturers of certain over-the-counter remedies warn that their products should not be used for more than three days. Also, the use or abuse of these drugs has resulted in anosmia, prolonged nasal obstruction, and habituation of the medications.

Other nasal sprays in the art include saline nasal sprays and topical steroid sprays. It is thought that the anti-inflammatory effect of steroid sprays produces a beneficial reaction in the nasal and sinus mucosa. However, such sprays can produce mucosal atrophy in post surgical states, and are generally effective only in reducing inflammation. They generally have inconsequential decongestant or physiological mucosal effects in mobilizing secretions or stimulating cells to evacuate secretions.

Another drawback of the prior art preparations is that a significant segment of the population is reluctant to apply artificial compositions to their nasal mucosa. As a result, topical therapy for nasal and sinus dysfunction in this segment of the population is largely nonexistent.

Attempts have been made to produce natural remedies for certain ailments. For instance, Stammberger has administered capsaicin P (trans-8-methyl-N-vanillyl-6-nonenamide), the pungent extract of red pepper, to patients with headaches. However, the capsaicin has been found to produce only profound vasodilation, sneezing, and either vasomotor or cholinergic secretory episodes. Also, the capsaicin is known to destroy unmyelinated C fibers of sensory and vagal afferent neurons.

Attempts have also been made to provide oral horseradish remedies for certain ailments. Mays, U.S. Pat. No. 98,875, relates to a medical compound for alleviating and curing asthma, coughs and colds. The compound includes pulverized horseradish. Diets, U.S. Pat. No. 74,205, discloses a medical compound containing horseradish for the cure of consumption. These oral horseradish remedies include substances, such as apple cider, ground ivy, and red beets, that are not suitable for topical applications.

Other natural oral remedies are known in the art. Reeves, U.S. Pat. No. 28,904, relates to a treatment for inflammatory diseases of the pulmonary organ that includes the use of capsaicin or African cayenne pepper. Greene, U.S. Pat. No. 378,504, relates to a catarrh treatment which includes red pepper (capsaicin).

However, none of the above-cited prior art provides a topical therapy or a preparation which is consistently safe and effective in the treatment of most nasal and sinus dysfunctions.

SUMMARY OF THE INVENTION

This invention provides a formulation for the topical treatment of nasal or sinus dysfunction, comprising an aqueous dispersion of a therapeutic amount of horseradish particles, sinigrin or allyl isothiocyanate in a dilute suspension or solution, e.g., in an aqueous saline suspension or solution.

Another aspect of the present invention relates to a method of making a horseradish dispersion useful in the treatment of nasal or sinus dysfunction. The method comprises (a) reducing the size of the horseradish to form horseradish particles of about 100–1000 microns; (b) dispersing the horseradish particles in a sodium chloride solution; (c) filtering the dispersion to obtain a filtrate comprising horseradish particles with a mean particle diameter from 20–90 microns dispersed in the sodium chloride solution; and (d) ultrafiltering the filtrate to obtain a horseradish dispersion comprising horseradish particles having a mean particle diameter not greater than 20 microns; wherein the horseradish dispersion comprises from about 0.01–10.0 weight percent horseradish.

DETAILED DESCRIPTION OF THE INVENTION

The present invention is useful in the treatment of a wide range of nasal and sinus dysfunctions. Such dysfunctions may occur prior or subsequent to surgery of the paranasal sinuses. Nasal and sinus dysfunctions may accompany allergic and vasomotor inflammatory conditions of the nasal mucous membrane. Certain mucous membrane disorders are associated with sinugenic headaches, post nasal discharge, and mucous membrane disorders presumably related to an immotile cilia condition. The latter condition results when the cilia of the mucous membranes lining the nose (pseudo-stratified ciliated columnar epithelium) appear to perform their mucous clearance and secretional mobilization activities in a sluggish or incomplete fashion. Immotile cilia conditions are frequently found in patients with chronic sinusitis, allergy, asthma, and other systemic conditions in which the nose and sinuses play a major role.

Nasal and sinus dysfunctions are sometimes a result of limited mucosal contact within the nose, resulting from nasal septal deviations, middle turbinate "squeeze" syndromes, and other "trigger" type situations that produce long-standing headaches, often projecting to remote dermatromes of the head and neck.

Other types of nasal and sinus dysfunctions that may be treated according to the present invention include nasal congestion from allergic, vasomotor, or infectious etiologies, and crusting or atrophic rhinitides associated with infection or surgery.

The preparations of the present invention may vary widely in composition, however they will typically comprise horseradish, sinigrin, allyl isothiocyanate, or mixtures thereof, in a saline solution.

Topical applications may be performed by a number of techniques. A preparation may be sprayed onto the affected mucosa, or the nasal mucosa may be bathed with drops of the preparation. A preparation may be applied by loading the preparation onto a swab and dabbing the swab on affected mucosao A preparation may also be applied as a nasal douche.

The preparations of the present invention preferably are derived from natural sources, although chemical synthesis of the active ingredients may also be employed. Horseradish (*raphanus rusticanus*) is the root of *radicula armoracia*. It contains ascorbic acid and sinigrin. Black mustard (also referred to as brown mustard and red mustard) is derived from dried ripe seeds of *brassica nigra*. Its constituents include sinigrin, myosin, sinapine, sulfocyanate and fixed oil (erucic, behenic and sinapolic acids.)

Sinigrin (1-thio-$\beta$-D-glucopyranose 1-(N-(sulfo-oxy)-3-butenimidate)) monopotassium salt can be isolated from black mustard seeds and from horseradish. It is commercially available under catalogue number 5-330-5 sold by Aldrich Chemical Company, Inc. Sinigrin preferably is derived from natural sources such as horseradish or black mustard. Sinigrin yields allyl isothiocyanate on hydrolysis with peroxidase or myrosinase, the latter being an enzyme found in black mustard. It is freely soluble in water, and has the following chemical formula:

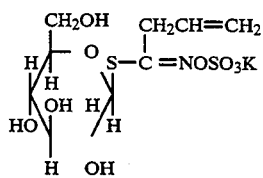

Allyl isothiocyanate (3-Isothiocyanato-1-propene) is commercially available under catalogue number A3,320-5 sold by Aldrich Chemical Company, Inc. Preferably it is derived from natural sources such as horseradish, black mustard, or cabbage. It can also be prepared from allyl iodide and potassium thiocyanate. Allyl isothiocyanate is of particular interest because it is considered to be the active moiety of horseradish, It has been described as the volatile oil of mustard (*Clinical Toxicology of Commercial Products*, Williams and Wilkins, reference 1359, Fifth Edition 1985). Allyl isothiocyanate has been used as a counter-irritant in medicine, as a fungicide, as an insecticidal fumigant, and as a repellent for cats and dogs. It is included in some model airplane cements at concentrations of 0.25-0.5% to deter "glue sniffing." It is a violent irritant unless either diluted or in its natural conjugated form, as in horseradish. It is used externally as a rubefacient (0.1 to 0.2% in 50% methanol). Allyl isothiocyanate is slightly soluble in water, and has the following formula:

Although the mode of operation of the present invention is not fully understood, it is believed that the beneficial effect of the preparations of the present invention may result from stimulating a focal physiological cellular response in mucosa. A natural antibiotic effect may result when either sinigrin or allyl isothiocyanate, perhaps in combination with ascorbic acid (vitamin C), is applied to affected mucosa. Vitamin C is present in large concentrations in horseradish.

The concentration of horseradish in the dispersion may vary. The concentration should be such that the user's mucosa do not become irritated, and generally is from about 0.01-10.0 weight percent horseradish. A preferred concentration is from about 3.0-10.0 weight percent, and a more preferred concentration is from about 8.0-10.0 weight percent horseradish.

The mean particle diameter of the horseradish should be small enough so that the user's mucosa do not become irritated. typically not in excess of 20 microns. A preferred mean particle diameter is from about 2-10 microns.

The concentration of sinigrin in the sinigrin solution may vary. The concentration should be such that the user's mucosa do not become irritated, and generally is from about 0.01-10.0 weight percent sinigrin. A preferred concentration is from about 5.0-10.0 weight percent, and a more preferred concentration is from about 8.0-10.0 weight percent sinigrin.

The concentration of allyl isothiocyanate in the isothiocyanate solution may vary. The concentration should be such that the user's mucosa do not become irritated, generally from about 0.01-2.0 weight percent allyl isothiocyanate. A preferred concentration is from about 0.05-2.0 weight percent, and a more preferred concentration is from about 0.05-1.5 weight percent allyl isothiocyanate.

The pH of the horseradish, sinigrin, and allyl isothiocyanate preparations should be such that the user's mucosa do not become irritated. A preferred pH is from about 5-7, and especially preferred is a pH of from about 6-7.

Sodium chloride in aqueous solution may desirably be present in the preparations of the present invention. The sodium chloride will generally be present in concentrations about 0.5-0.8% by weight, preferably from about 0.6-0.7%, and especially preferably about 0.65% weight percent sodium chloride. Other salts may optionally be utilized, such as potassium salts and/or magnesium salts.

The preparations of the present invention will generally be applied periodically as necessary to treat nasal and sinus dysfunctions. About 2-10 ml of 0.01-10.0 weight percent horseradish or sinigrin preparation may be applied to affected mucosa every three hours. Preferably, about 5-10 ml of 8-10 weight percent horseradish will be applied once every 6-12 hours. About 2-10 ml of 0.01-2.0 weight percent allyl isothiocyanate solution may be applied to affected mucosa every 3 hours. Preferably, about 5-10 ml of 1.0-2.0 weight percent allyl isothiocyanate will be applied once every 6-12 hours.

The method of making the horseradish dispersion includes ultrafiltering a combination of horseradish and saline solution. Ultrafiltering may be performed by a variety of techniques, such as with medium porous Fisher filter paper having a 5 to 10 micron retention rating; a Gelman membrane filter with a thick, nominal rating and a retention rating of 2 microns; or a Whatman filter number 40 having an 8 micron retention rating.

The preparations of the present invention may contain other active or inert ingredients. For instance, ascorbic acid may be present. Ascorbic acid is beneficial because of its salutary effects on mucous membranes, and it may be present in concentrations of from about 0–10.0%, preferably from about 0.01–5.0%, and especially preferably from about 0.1–4.0% by weight. A buffer may be present. Preservatives such as ethyl alcohol may also be present.

CLINICAL TESTS

Horseradish sprays were produced and clinically tested on patients having a wide range of nasal and sinus dysfunctions.

Batches of horseradish spray were prepared as described below: Horseradish was first reduced in size to about 100–1000 microns. 270 grams were placed in a steel beaker with 1500 cc of 0.6% sodium chloride solution (aqueous). Ethyl alcohol was then added in such amounts that the resulting dispersion contained either 0.02%, 0.03% or 0.04% ethyl alcohol by weight.

The mixtures were then mechanically shaken for one minute and filtered through a number 20 wire mesh. They were then ultra filtered through medium filter paper and placed in sterile plastic spray bottles. The mean particle diameter of the horseradish particles in the dispersions was approximately 10 microns. The resulting dispersions contained horseradish in concentrations of from about 8.0–10.0 percent by weight.

The horseradish dispersions were prescribed to 100 patients with postoperative healing mucous membrane states, allergic rhinitis, vasomotor rhinitis, sinugenic headache syndromes, and other inflammatory mucosal disease states. Patients who had failures of other forms of therapy, or who had undergone sinus or nasal surgery were utilized in the study after being informed that the method and spray were experimental and should not be considered their primary mode of therapy. The prescribed rate of topical application was twice daily in each nostril. The dispersions were applied by spraying approximately 5 ml of the dispersion onto affected mucosa.

Ninety-five percent of the treated patients showed good to excellent results from the treatment. Results were measured in terms of mobilization of crusts following surgery, accelerated postoperative healing following nasal and sinus surgeries, relief of congestion with improvement in inflammation in patients in vasomotor and allergic states and in patients with the common cold.

One patient reported a return of his sense of smell after 15 years and multiple surgeries. Most patients reported improvement in their nasal airway, freedom from crusting and moderate to marked relief of sinusitis-induced headaches.

In some of the patients, two or more dysfunctional categories had coexisted. These included combinations of postoperative healing states, sinugenic headaches, vasomotor rhinitis, nasal congestion, crushing rhinitis, and allergic rhinitis. In many cases, all of the dysfunctional categories in these patients were alleviated.

There were no instances of toxicity, or interference with other forms of therapy. No undesirable side effects were exhibited, such as degradation of nasal mucous membranes or worsening of nasal or sinus conditions. No hypersensitivity or allergic reactions were noted. Only five patients reported no improvement in symptoms.

Variations and modifications of the present invention will be apparent to those skilled in the art. For example, the preparations may contain vitamins other than vitamin C. The following claims are intended to cover all such variations and modifications falling within the spirit and scope of the invention.

I claim:

1. A formulation for the treatment of nasal or sinus dysfunction comprising an aqueous salt dispersion of solid horseradish particles having a mean particle diameter not greater than 20 microns, said dispersion containing from 0.01 to 10.0 weight percent of the horseradish particles.

2. The formulation of claim 1, wherein the mean particle diameter of the horseradish particles is from 2–10 microns.

3. The formulation of claim 1, wherein the pH of the dispersion is from 5–7.

4. The formulation of claim 1, wherein the dispersion contains from 0.6–0.7 weight percent sodium chloride.

5. The formulation of claim 1, wherein the dispersion of horseradish particles contains from 3.0 to 10.0 weight percent of horseradish particles having a mean particle diameter of from 2–10 microns.

6. The formulation of claim 1, wherein the dispersion of horseradish particles contains from 8.0–10.0 weight percent of horseradish particles having a mean particle diameter of from 2–10 microns.

7. The formulation of claim 1, containing from 0.5–0.8% by weight of a dissolved salt selected from the group consisting of sodium chloride, a potassium salt, a magnesium salt and mixtures thereof.

8. The formulation of claim 1, wherein the dispersion contains sodium chloride.

9. The formulation of claim 8, wherein the dispersion contains from 0.5 to 0.8 weight percent sodium chloride.

10. The formulation of claim 1, comprising an aqueous saline dispersion of horseradish particles having a mean particle diameter not greater than 20 microns, said dispersion containing from 0.01 to 10.0 weight percent of the horseradish particles and from 0.5 to 0.8 weight percent sodium chloride.

* * * * *